United States Patent [19]

Perka

[11] 4,316,454
[45] Feb. 23, 1982

[54] THERAPEUTIC POSITIONING DEVICE
[76] Inventor: Francis A. Perka, 3314 Arundel Ave., Alexandria, Va. 22306
[21] Appl. No.: 181,334
[22] Filed: Aug. 25, 1980
[51] Int. Cl.³ .............................................. A61F 5/10
[52] U.S. Cl. .................................................... 128/77
[58] Field of Search ............... 128/80 R, 82, 83, 87 R, 128/87 C, DIG. 6, DIG. 15, 77; 272/67

[56] References Cited
U.S. PATENT DOCUMENTS

| | | | |
|---|---|---|---|
| 1,296,722 | 3/1919 | Washburn | 128/82 |
| 1,879,401 | 9/1932 | Monaco | 272/67 |
| 1,880,945 | 10/1932 | Ettinger | 128/87 R |
| 3,480,013 | 11/1969 | Garber | 128/DIG. 6 |
| 3,568,671 | 3/1971 | Graham | 128/87 R |
| 3,903,878 | 4/1975 | Spann | 128/80 R |

Primary Examiner—John D. Yasko
Attorney, Agent, or Firm—Leitner, Palan, Martin & Bernstein

[57] ABSTRACT

A therapeutic positioning device for a paralyzed limb having either a flaccid or spastic condition. The therapeutic device consists of a support board removably accommodating a positioning rod which maintains the paralyzed limb in a therapeutically desirable position. The support board is provided with several locating holes each accepting the positioning rod. The locating holes are placed on the support board such that the rod can be located at varying positions to achieve the optimal therapeutic effect for a variety of limb sizes and conditions.

7 Claims, 7 Drawing Figures

U.S. Patent  Feb. 23, 1982  4,316,454
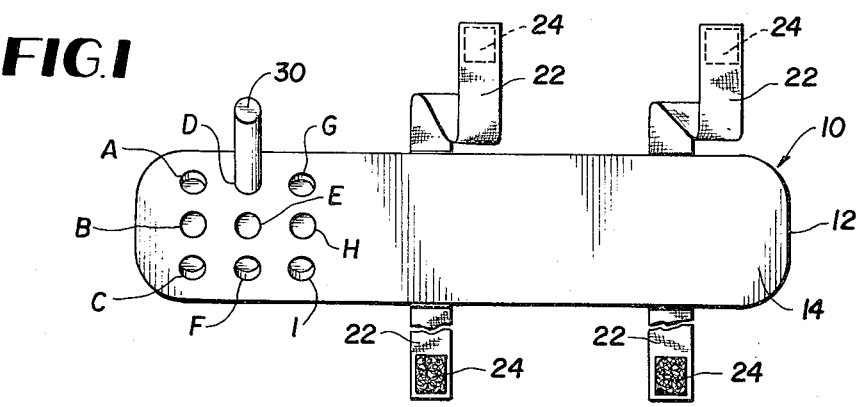
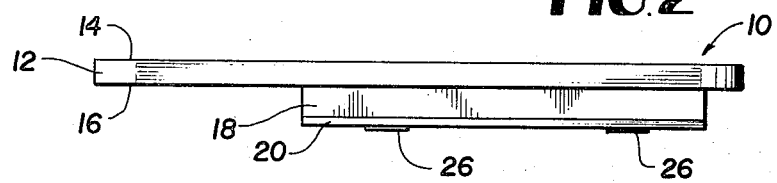
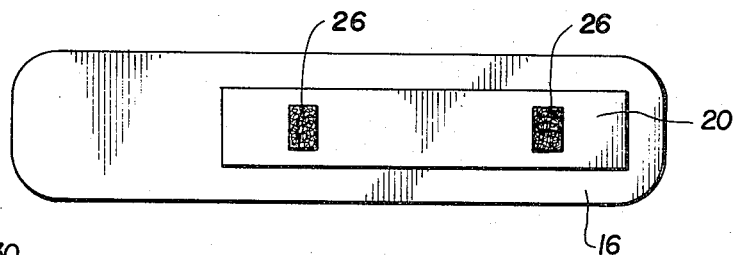
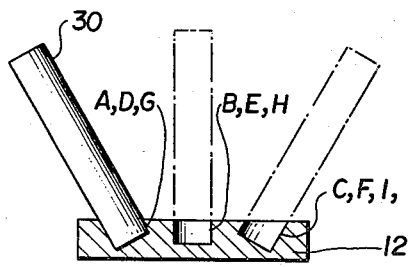
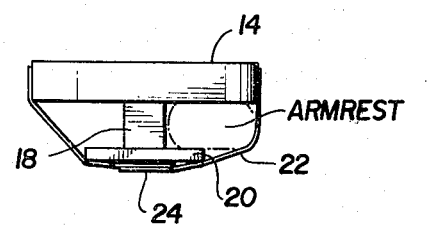
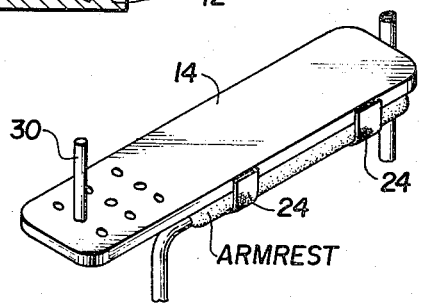
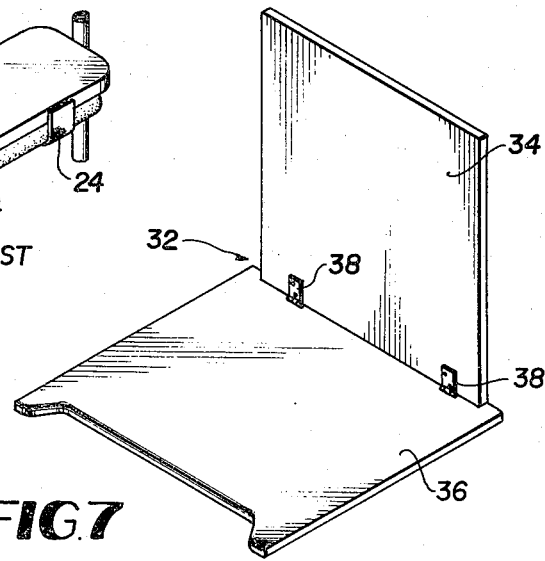

THERAPEUTIC POSITIONING DEVICE

FIELD OF INVENTION

The present invention relates generally to the field of rehabilitation and more particularly to a device used for therapeutic positioning of a paralyzed limb of a patient.

BACKGROUND OF INVENTION

Patients suffering from paralysis of one or more limbs, as is commonly caused by a stroke, central nervous dysfunction, or other neurological disorder are unable to bear weight on or otherwise use the affected limb. The paralyzed limb is either in a condition of flaccidity wherein there is very little or no tone in the muscles resulting in the limb having a hanging or limp condition or spasticity wherein there is too much tone or tonic spasms in the muscles resulting in the limb assuming an abnormal position. Left untreated both such conditions can and often do cause other difficulties to the patient such as unbalanced posture, limitation of joint movement, deformity of the limb, and atrophy. A patient suffering from a central nervous system dysfunction and confined to a wheelchair in most instances loses the ability to shift and bear body weight on the affected side which results in severe discomfort and asymmetry of the body including the spinal column.

Heretofore no simple and inexpensive device has been available that serves to both relieve the discomfort caused by a central nervous system dysfunction in a limb (arm or leg) of a patient and help normalize the muscle tone of either a spastic or flaccid condition especially for a person confined to a sitting position. Conventional devices are either very complex in design and expensive or both. U.S. Pat. No. 3,903,878 to Spann issued on Sept. 9, 1975, is an example of a prior art device used to support the limb of a bedridden patient. Spann recognizes the value of maintaining the limbs of a bedridden patient in a normalized muscle tone condition by providing a device that serves to support the limb for comfort and physical muscle tone therapy. The Spann device, however, is not directed to a person suffering from a paralyzed arm or leg such as one with a central nervous system dysfunction exhibiting spasticity. Further, the device does not provide the necessary support for proper body posture for a person confined to a sitting position.

Other examples of prior art are U.S. Pat. No. 1,879,401 to Monaco issued on Sept. 27, 1932, and U.S. Pat. No. 3,605,733 to Sukle issued on Sept. 20, 1971, wherein exercise devices for paralyzed limbs are described. Monaco recognized that systematic exercise of a paralyzed limb can result in the patient having increased use of the muscles of that limb and provides a means wherein the paralyzed hand and arm of a patient can be exercised by placing the patient's fingers between spaced vertical pegs and using the other hand to move the fingers up and over the peg into the next adjacent space. In the Sukle patent a therapeutic device for the paralyzed hand and arm of a stroke patient is provided having a continuous reciprocating moving belt upon which the paralyzed limb is placed for exercise.

The above noted patents represent the type of relevant exercise devices known in the art. It will be appreciated that prior to the instant invention no exercise or therapeutic device provided a means of maintaining proper body posture, comfortable support and adjustable positioning means tending to alleviate either a flaccid or spastic condition.

SUMMARY OF THE INVENTION

An object of the present invention is to provide a therapeutic muscle positioning device for a person having a paralyzed or otherwise immovable limb, such device being simple in design and inexpensive to manufacture.

A further object of the invention is a therapeutic positioning device that provides a comfortable support and adjustable positioning means to a paralyzed or otherwise immovable limb of a person having a flaccid or spastic condition so as to help alleviate some of the consequences of such condition.

A still further object of the invention is to provide a therapeutic positioning device for a paralyzed arm of a person confined to a sitting position that helps maintain proper body posture and serves as a comfortable support.

Accordingly, this therapeutic device accomplishes the above objectives by:

1. Providing a means for supporting a paralyzed or otherwise immovable limb.
2. Providing a positioning means in the form of a generally vertical extending rod, capable of being placed in a plurality of locations on a support board to accomodate the size or length of a person's limb, and which ensures optimal positioning of a spastic or flaccid arm. In the preferred embodiment the support board is removably attached to the arm rest of a wheelchair and used by a person having a paralyzed arm and confined to a sitting position a majority of his waking hours.

Other objects, advantages, and novel features of the present invention will become apparent from the following detailed description of the invention when considered in conjunction with the accompanying drawings.

BRIEF DESCRIPTION OF THE DRAWINGS

FIG. 1 is a top plan view of a preferred embodiment of the inventive therapeutic positioning device.

FIG. 2 is a side plan view of the device shown in FIG. 1 without straps.

FIG. 3 is a bottom plan view of the device shown in FIG. 1 without straps.

FIG. 4 is a front plan view of the device shown in FIG. 1 without straps.

FIG. 5 is a cross-section of the support board of the device of FIG. 1 showing the outline of the holes therein and alternative positions of the positioning rod.

FIG. 6 is a perspective view of the device mounted on the arm rest.

FIG. 7 is a perspective view of a sitting support board used in conjunction with the device.

DESCRIPTION OF PREFERRED EMBODIMENT

Referring to the drawings, therapeutic positioning device 10 illustrates the preferred embodiment of the invention wherein support board 12 is provided with an upper surface 14 having holes A thru I located therein. A greater or lesser number of holes may be provided, it not being intended to limit the invention to a support board with any specific number of holes. Bottom surface 16 of support board 12 has attached thereto mounting boards 18 and 20 as best seen in FIG. 4. Attached to the sides of support board 12 are straps 22 having Velcro patches 24 best illustrated in FIG. 1. Velcro patches 26 are provided on the bottom surface of mounting board 20.

The device 10 can be mounted on an armrest of a wheelchair or other appropriate location for use with either the left or right arm. The device is positioned on the armrest such that bottom surface 16 of support board 12 and the upper surface of mounting board 20 surround the armrest as shown in FIG. 4 wherein the armrest is shown in phantom. Straps 22 are wrapped around the armrest with Velcro patches 24 being connected to a respective Velcro patch 26 resulting in a stabilized mounting of the device 10.

A positioning rod 30 is provided and is removably inserted in any of the holes A thru I. For reasons to be explained in greater detail below, holes A, D and G located along one side of support board 12 are formed on an angle as best seen in FIG. 5; holes C, F and I located along the other side of support board 12 are formed on an angle in an opposing direction also best illustrated in FIG. 5 and holes B, E and H are formed along the middle longitudinal axis of support board 12.

In use, device 10 is mounted, for example, on the right-hand armrest of a wheelchair. The paralyzed right arm of a person is placed directly on surface 14 of support board 12 such that the hand is located in the vicinity of holes A thru I and the elbow is rested on the other end thereof. The muscles of the forearm of a person having a spastic condition may have a tendency to exhibit a pronated position, that is a position in which the forearm tends to rotate toward the mid-line of the body. In that event, rod 30 is placed in the appropriate hole A thru I depending on the length of the person's arm, and the person's hand is placed such that the hand is placed directly next to and if possible in a holding position around rod 30. Due to the interaction of the rod 30 providing contact to the metacarpal phalangeal joint, the therapeutic effect over a prolonged time being a tendency toward reduction in muscle tone.

In the instance wherein the arm of a patient is in supination or a rotation away from the mid-line of the body, the rod 30 is placed in appropriate hole A thru I and the hand is placed so that supination is prevented. Holes A, D and G are so positioned that rod 30 when inserted therein will be at an angle to surface 14 of support board 12 as best seen in FIG. 5. Holes C, F, and I are angled as shown in FIG. 5 so that rod 30 when inserted therein will be at an opposing angle. The purpose of providing rod 30 at angles as shown in FIG. 5 is to increase its effect on a patient suffering from severe spasticity or flaccidity.

A seat and back-rest support 32 may be provided as seen in FIG. 7 having a back-rest member 34 and seat member 36 connected by hinges 38. Any suitable attachment means may be provided for use, as an example, on a wheelchair. The purpose of the seat and back-rest support 32 is to provide a firm support for the patient's body such that when arm support device 10 is used, the patient is maintained in a balanced and proper body posture position.

From the preceding description of the preferred embodiment, it is evident that a therapeutic positioning device is attained for a paralyzed arm of a patient suffering either a flaccid or spastic muscle condition and although the invention has been described and illustrated in detail, it is to be clearly understood that the same is by way of illustration and example only and is not to be taken by way of limitation, the spirit and scope of this invention being limited by the terms of the appended claims.

What is claimed is:

1. A therapeutic device used for positioning a limb against pronation or supination as may result from a spastic or a flaccid condition, respectively comprising:
    a support board for supporting said limb; and
    a limb positioning means extending from said support board for preventing limb pronation in the case of a spastic limb or limb supination in the case of a flaccid limb,
    wherein said support board is provided with a plurality of integrally formed adjustment means for varying the physical relationship between the support board and the limb positioning means and wherein said limb positioning means is removably mounted on said support board in any one of said plurality of integrally formed adjustment means.

2. In a therapeutic device consisting of a limb positioning device as claimed in claim 1, further including a seat and back rest support cooperating with a wheel chair for providing a firm support for a patient's body such that when the limb positioning device is used the patient is maintained in a balanced and proper body posture position.

3. The device of claim 1 wherein said support board is a portable flat surface.

4. The device of claim 3 wherein said limb positioning means is a rod and said plurality of integrally formed adjustment means are holes located in said support board into which said limb positioning means is positioned.

5. The device of claim 1 including means for mounting and attaching said device to an armrest.

6. The device of claim 3 wherein said mounting and attaching means includes straps connected to said 1st means.

7. The device of claim 6 wherein said mounting and attaching means further includes a mounting board attached in a spaced parallel relationship to said support board such that said mounting board and said support board sandwiches the armrest upon which it is mounted so as to provide a stabilized mounting.

* * * * *